United States Patent
Senegas et al.

(10) Patent No.: US 9,568,578 B2
(45) Date of Patent: Feb. 14, 2017

(54) MAGNETIC RESONANCE EXAMINATION SYSTEM WITH PREFERRED SETTINGS BASED ON DATA MINING

(75) Inventors: Julien Senegas, Hamburg (DE); Jens Von Berg, Hamburg (DE); Eric Cohen-Solal, Ossining, NY (US); Sebastian Peter Michael Dries, Hamburg (DE); Michael Chun-Chieh Lee, Bronx, NY (US); Tim Nielsen, Hamburg (DE); Stefanie Remmele, Hamburg (DE); Torbjorn Vik, Hamburg (DE)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 822 days.

(21) Appl. No.: 13/993,088

(22) PCT Filed: Dec. 7, 2011

(86) PCT No.: PCT/IB2011/055511
§ 371 (c)(1),
(2), (4) Date: Jun. 11, 2013

(87) PCT Pub. No.: WO2012/080904
PCT Pub. Date: Jun. 21, 2012

(65) Prior Publication Data
US 2013/0265044 A1  Oct. 10, 2013

(30) Foreign Application Priority Data
Dec. 13, 2010 (EP) .................................... 10194733

(51) Int. Cl.
*G01R 33/54* (2006.01)
*G06F 19/00* (2011.01)

(52) U.S. Cl.
CPC .......... *G01R 33/543* (2013.01); *G01R 33/546* (2013.01); *G06F 19/321* (2013.01); *G06F 19/325* (2013.01)

(58) Field of Classification Search
USPC ... 324/300–322; 600/407–435; 382/128–131
See application file for complete search history.

(56) References Cited

U.S. PATENT DOCUMENTS 6,801,037 B1 * 10/2004 Zhang .................... G01R 33/54
                                                                                      324/309
7,081,750 B1 *  7/2006 Zhang .................... G01R 33/54
                                                                                      324/309

(Continued)

FOREIGN PATENT DOCUMENTS

| EP | 1229472 A1 | 8/2002 |
| EP | 1354554 A2 | 10/2003 |
| WO | 03021284 A1 | 3/2003 |

OTHER PUBLICATIONS

Marusina et al "Modern Types of Tomography" Textbook St Peterburg, 2006 p. 57-63 (no English language equivalent available) translation of RU office action in corresponding application provided.

*Primary Examiner* — Melissa Koval
*Assistant Examiner* — Tiffany Fetzner

(57) ABSTRACT

A magnetic resonance imaging scan using a MR scanner receives via a user interface a MR imaging protocol categorizable into a MR scan type of a predefined set of MR scan types. Further, a database is queried by providing to the database scan information permitting the database to identify the MR scan type of the MR imaging protocol. Statistical information on the MR scan type which can include statistics on modifications of individual scan parameters of the MR scan type is received from a database, and the statistical information is provided to the user interface.

(Continued)

Modifications of the MR imaging protocol can be received from the user interface, resulting in a modified MR imaging protocol, according to which the MR imaging scan can be performed.

18 Claims, 2 Drawing Sheets

(56) References Cited

U.S. PATENT DOCUMENTS

| | | |
|---|---|---|
| 7,152,785 B2 | 12/2006 | Metz |
| 7,315,755 B2 | 1/2008 | Tsunoda |
| 7,542,792 B2 | 6/2009 | Wollenweber |
| 7,725,154 B2 | 5/2010 | Beck |
| 8,422,820 B2 * | 4/2013 | Zbilut ............... G06K 9/00523 382/128 |
| 8,975,892 B2 * | 3/2015 | Flammang ............ G01R 33/50 324/307 |
| 2002/0186818 A1 * | 12/2002 | Arnaud ................. A61B 6/583 378/165 |
| 2004/0148403 A1 | 7/2004 | Choubey |
| 2005/0271297 A1 * | 12/2005 | Zbilut ................ G06K 9/00523 382/278 |
| 2006/0173663 A1 * | 8/2006 | Langheier ........... G06F 19/3437 703/11 |
| 2008/0097794 A1 * | 4/2008 | Arnaud ................. A61B 6/583 705/3 |
| 2008/0130972 A1 | 6/2008 | Miller |
| 2009/0080725 A1 * | 3/2009 | Zbilut ................ G06K 9/00523 382/128 |
| 2009/0254572 A1 * | 10/2009 | Redlich .................. G06Q 10/06 |
| 2013/0141092 A1 * | 6/2013 | Flammang .......... G01R 33/543 324/309 |
| 2013/0265044 A1 * | 10/2013 | Senegas .............. G01R 33/543 324/307 |
| 2014/0320126 A1 * | 10/2014 | Heaton ................. G01V 11/00 324/303 |

* cited by examiner

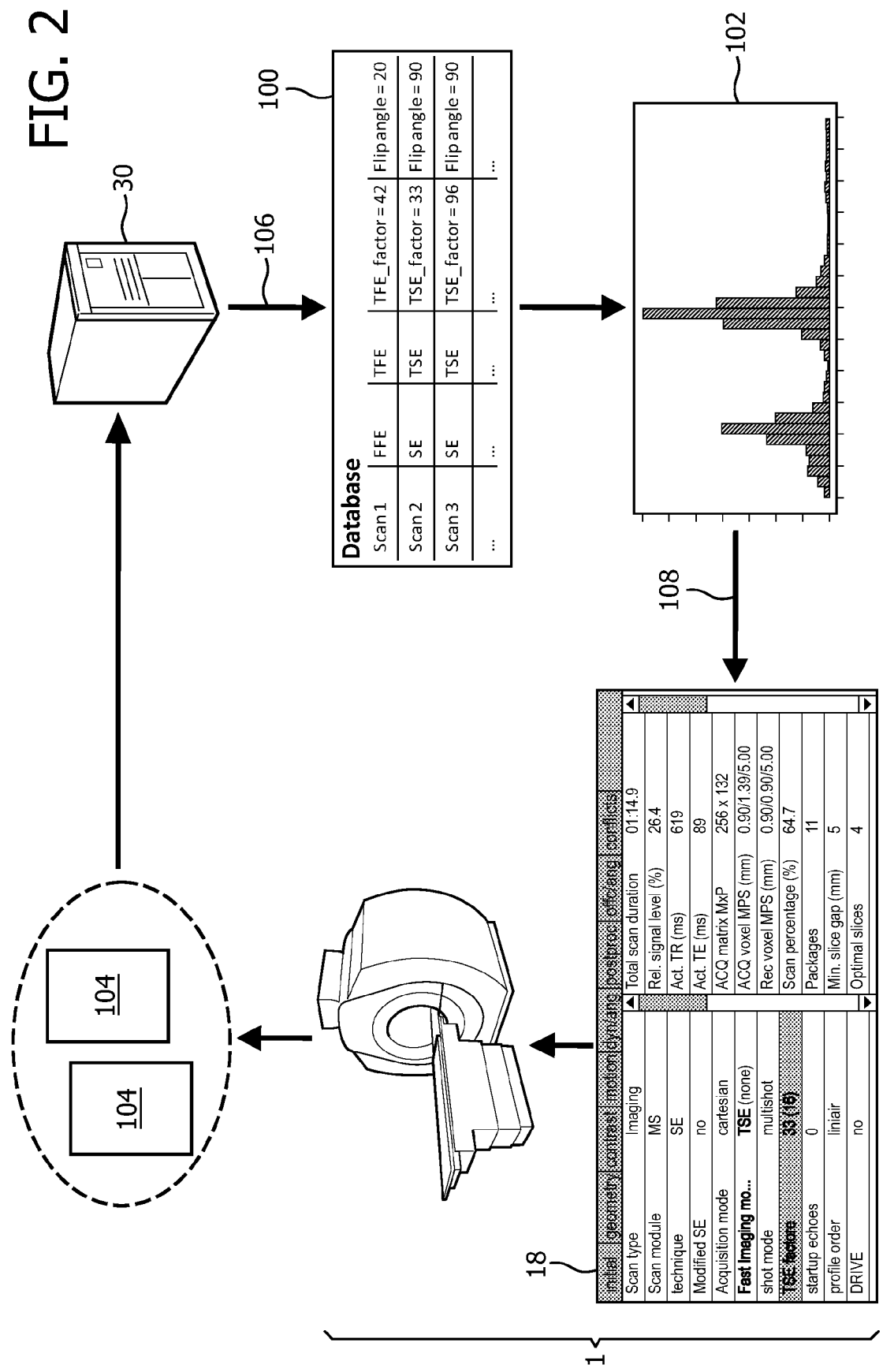

MAGNETIC RESONANCE EXAMINATION SYSTEM WITH PREFERRED SETTINGS BASED ON DATA MINING

CROSS-REFERENCE TO PRIOR APPLICATIONS

This application is the U.S. National Phase application under 35 U.S.C. §371 of International Application No. PCT/IB2011/055511, filed on Dec. 7, 2011, which claims the benefit of European Patent Application No. 10194733.1, filed on Dec. 13, 2010. These applications are hereby incorporated by reference herein.

FIELD OF THE INVENTION

The invention relates to a method of performing a magnetic resonance imaging scan using an MR scanner, a method of providing statistical information to a magnetic resonance imaging scanner, a computer program product, a magnetic resonance imaging scanner for performing a magnetic resonance imaging scan and a database system.

BACKGROUND OF THE INVENTION

Image-forming MR methods, which utilize the interaction between magnetic field and nuclear spins in order to form two-dimensional or three-dimensional images are widely used nowadays, notably in the field of medical diagnostics, because for the imaging of soft tissue they are superior to other imaging methods in many respects, they do not require ionizing radiation, and they are usually not invasive.

According to the MR method in general, the body of a patient or in general an object to be examined is arranged in a strong, uniform magnetic field BO whose direction at the same time defines an axis, normally the z-axis, of the coordinate system on which the measurement is based.

The magnetic field produces different energy levels for the individual nuclear spins in dependence on the applied magnetic field strength which spins can be excited (spin resonance) by application of an alternating electromagnetic field (RF field) of defined frequency, the so called Larmor frequency or MR frequency. From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicularly to the z-axis, so that the magnetization performs a precessional motion about the z-axis.

Any variation of the magnetization can be detected by means of receiving RF antennas, which are arranged and oriented within an examination volume of the MR device in such a manner that the variation of the magnetization is measured in the direction perpendicularly to the z-axis.

In order to realize spatial resolution in the body, switching magnetic field gradients extending along the three main axes are superposed on the uniform magnetic field, leading to a linear spatial dependency of the spin resonance frequency. The signal picked up in the receiving antennas then contains components of different frequencies which can be associated with different locations in the body.

The signal data obtained via the receiving antennas corresponds to the spatial frequency domain and is called k-space data. The k-space data usually includes multiple lines acquired with different phase encoding. Each line is digitized by collecting a number of samples. A set of samples of k-space data is converted to an MR image, e.g. by means of Fourier transformation.

The above description of performing magnetic resonance imaging provides a brief impression on the plurality of parameters which may be adjusted in order to obtain an MR image of a desired portion of the object to be imaged at a desired quality.

Typically, an MR scan protocol used for adjustment of the conditions to be used when performing a magnetic resonance imaging scan can consist of more than 150 adjustable parameters. With the continuing advances in MR sequence development, it is expected that even more methods become available and need to be parameterized in the user interface used at the MR scanner to provide the relevant MR scan protocol parameters to the scanner.

Moreover, radiologists and technicians frequently need to work on different MR systems, from different vendors and are familiar with the user interface of a presently used MR system only up to a certain degree. As a consequence, in these conditions the optimal choice of scan parameters is a difficult, tedious and often iterative task, even for expert users. As a consequence, many scans need to be repeated until image quality is judged good enough. In other cases, the appropriate choice of scan parameters results in inferior image quality below the requested quality standards. Another consequence is that advanced imaging techniques are not used as often as they could be, because the technician may not be aware of the suitable techniques to solve a particular image quality problem or to address a particular patient imaging need.

U.S. Pat. No. 7,315,755 discloses a system and method for communicating a protocol over a network. More specifically, this document relates to a protocol/medical image registration method that permits centralized management of pairs of protocol and a medical image, wherein numerous user terminals are permitted to share protocols as common resources. Consequently, this method permits to make imaging protocols available, however with the drawback that only 'prefabricated' protocols are provided, such that with respect to the individual circumstances with respect to an imaging procedure a user is still required to adapt the scan parameters of the selected MR scan protocol in an individual manner. Consequently, the optimal choice of scan parameters is still difficult even for expert users.

From the foregoing it is readily appreciated that there is a need for an improved method of performing a magnetic resonance imaging scan. Further, there is a need for an improved magnetic resonance imaging scanner and an improved computer program product.

SUMMARY OF THE INVENTION

In accordance with the invention, a method of performing a magnetic resonance imaging scan using an MR scanner is provided, wherein the method comprises receiving an MR imaging protocol via user interface, the MR imaging protocol being categorizable into an MR scan type of a predefined set of MR scan types. Further, the method comprises querying a database by providing scan information to the database, the scan information permitting the database to identify the MR scan type of the MR imaging protocol. The method further comprises receiving a response to said querying from the database statistical information on the MR scan type, said statistical information comprising statistics on modifications of individual scan parameters of the MR scan type. Further, said statistical information is then provided to the user interface. In turn, modifications of said MR imaging protocol are received from the user interface, said modifications resulting in a modified MR imaging protocol. Finally, the MR imaging scan is performed using the modified MR imaging protocol.

It has to be noted that an 'MR scan type' is understood as for example a generic term which permits to describe a set of specific imaging sequences which can be classified with said generic term. For example, the generic term or MR scan type 'gradient echo' covers the pulse sequences coherent gradient echo (FFE), incoherent gradient echo (T1 FFE), incoherent gradient echo, steady-state free precession (T2 FFE), balanced sequence (balanced FFE), and double echo steady-state. In a further example, the MR scan type 'inversion recovery' covers short T1 inversion recovery (STIR), long Tau inversion recovery (FLAIR) and true inversion recovery (Real IR).

Further, an MR scan type may also categorize an MR imaging protocol with respect to different scan options used when performing an MR imaging scan. Options comprise for example the provision of saturation pulses for water and/or fat saturation, multi-slice imaging, single-slice imaging, three-dimensional imaging, bandwidth, magnetization transfer contrast, the application of partial echoes, as well as patient-specific protocols used for ECG synchronization, respiratory compensation and automatic bolus detection.

As a consequence, any MR imaging protocol received via the user interface can be categorized into a certain MR scan type which in turn permits to provide an elegant possibility to provide statistical information with respect to this MR scan type, wherein the statistical information was obtained by analysis of previous MR scans.

Consequently, the present invention provides a possibility to support for example a technician at a user interface with information on parameters which may require adaption when using the selected MR imaging protocol and which parameter values are typically used, i.e. are appropriate.

In accordance with an embodiment of the invention the statistical information is based on information about previously performed MR imaging scans employing said MR scan type. For example, providing said statistical information to the user interface may comprise indicating individual scan parameters for which the statistics on modification frequency is above a predefined threshold. In other words, the invention proposes to compute statistics on scan parameters which are most frequently adapted for a given MR scan type or protocol, wherein preferably the statistics are computed together with statistical descriptors of the parameter values, such as the modes (most frequent values), or the range. This information may then be provided to the user interface, i.e. for example displayed to the user in a suitable manner, for example while adjusting a given parameter.

In accordance with a further embodiment of the invention, the statistical information comprises statistics on ranges of modifications of individual scan parameters of the scan type. For example, the statistics on ranges of modifications of individual scan parameters of the MR scan type further comprise threshold ranges for said scan parameters. Thus, based on previously performed MR imaging scans, typical ranges of scan parameters are identified, such that a user may be assisted in selecting appropriate parameter values when adapting his imaging sequence by providing these ranges. Consequently, this prevents the user to accidentally enter unusual scan parameters which are completely 'out of range'.

In accordance with a further embodiment of the invention, the method further comprises receiving a modification of a scan parameter of the MR imaging protocol via the user interface, determining if the received modification of the scan parameter is outside a threshold range for said scan parameter and providing an indication to the user interface in case the received modification if outside the threshold range.

Additionally or alternatively it may be possible to provide for example the threshold ranges to the user interface which has the advantage that the user is assisted in choosing the most appropriate parameters since he will intuitively select the parameters to be within the threshold range.

In accordance with a further embodiment of the invention, the method further comprises providing information about the MR imaging protocol used in the imaging procedure to the database. Thus, this permits the database to use the imaging parameters used for the actual MR imaging scan to update its statistics with respect to the used MR scan type.

In accordance with a further embodiment of the invention, the method further comprises categorizing the MR imaging protocol for obtaining an MR scan type of the imaging protocol, wherein the scan information comprises the obtained MR scan type. In other words, either the MR scanner itself performs the categorization and only provides the resulting MR scan type to the database, or the MR scanner provides for example the MR imaging protocol itself to the database, wherein in turn the database performs the categorization of the MR imaging protocol to determine the MR scan type associated with said MR imaging protocol.

In accordance with an embodiment of the invention, the scan information comprises parameters of the MR imaging protocol and/or information on the MR scanner hardware and/or information on the MR scanner software. Consequently, this permits to identify the MR scan type more precisely adapted to the actual requirements with respect to hardware and software. Thus, besides scan protocol parameters, information on hardware and software configuration for each scan protocol like scanner type, applied magnetic field strengths, gradient type or software release number may be used to categorize in a highly precise manner the correct MR scan type.

In another aspect, the invention relates to a method of providing statistical information to a magnetic resonance imaging scanner, the method comprising receiving a query from a magnetic resonance imaging scanner, said query comprising scan information permitting the database to identify the MR scan type of an MR imaging protocol employed at a scanner for magnetic resonance imaging. The method further comprises generating statistical information on the MR scan type, said statistical information comprising statistics and modifications of individual scan parameters of the MR scan type, the statistical information being based on information about previously performed MR imaging scans employing said MR scan type, and providing to the magnetic resonance imaging scanner said statistical information.

In accordance with an embodiment of the invention, the received scan information comprises the MR imaging protocol, wherein the method further comprises categorizing the MR imaging protocol for obtaining the MR scan type of the MR imaging protocol. However, as mentioned above, categorizing for obtaining the MR scan type can also be performed at the MR scanner itself, such that directly the MR scan type is received at a database.

In accordance with a further embodiment of the invention, the statistical information is generated using data-mining.

In another aspect, the invention relates to a computer program product comprising computer executable instructions to perform the method steps as described above.

In another aspect, the invention relates to the magnetic resonance imaging scanner for performing the magnetic resonance imaging scan, the system being adapted to perform the following steps:
- receiving an MR imaging protocol via a user interface, the MR imaging protocol being categorizable into an MR scan type of a predefined set of MR scan types,
- querying a database by providing scan information to the database, the scan information permitting the database to identify the MR scan type of the MR imaging protocol,
- receiving in response to said querying from the database statistical information on the MR scan type, said statistical information comprising statistics on modifications of individual scan parameters of the MR scan type,
- providing said statistical information to the user interface,
- receiving modifications of said MR imaging protocol, said modifications resulting in a modified MR imaging protocol,
- performing the MR imaging scan using the modified MR imaging protocol.

In another aspect, the invention relates to a database system for providing statistical information to a magnetic resonance imaging scanner, the system being adapted for:
- receiving a query from a magnetic resonance imaging scanner, said query comprising scan information permitting the database to identify the MR scan type of an MR imaging protocol employed at the scanner for magnetic resonance imaging,
- generating statistical information on the MR scan type, said statistical information comprising statistics on modifications of individual scan parameters of the MR scan type, the statistical information being based on information about previously performed MR imaging scans employing said MR scan type
- providing to the magnetic resonance imaging scanner said statistical information.

BRIEF DESCRIPTION OF THE DRAWINGS

The enclosed drawings disclose preferred embodiments of the invention. It should be understood, however, that the drawings are designed for the purpose of illustration only and not as a definition of the limits of the invention. In the drawings:

FIG. 2 is a block diagram illustrating various method steps to perform the method according to the invention.

DETAILED DESCRIPTION OF EMBODIMENTS

Figure 1:
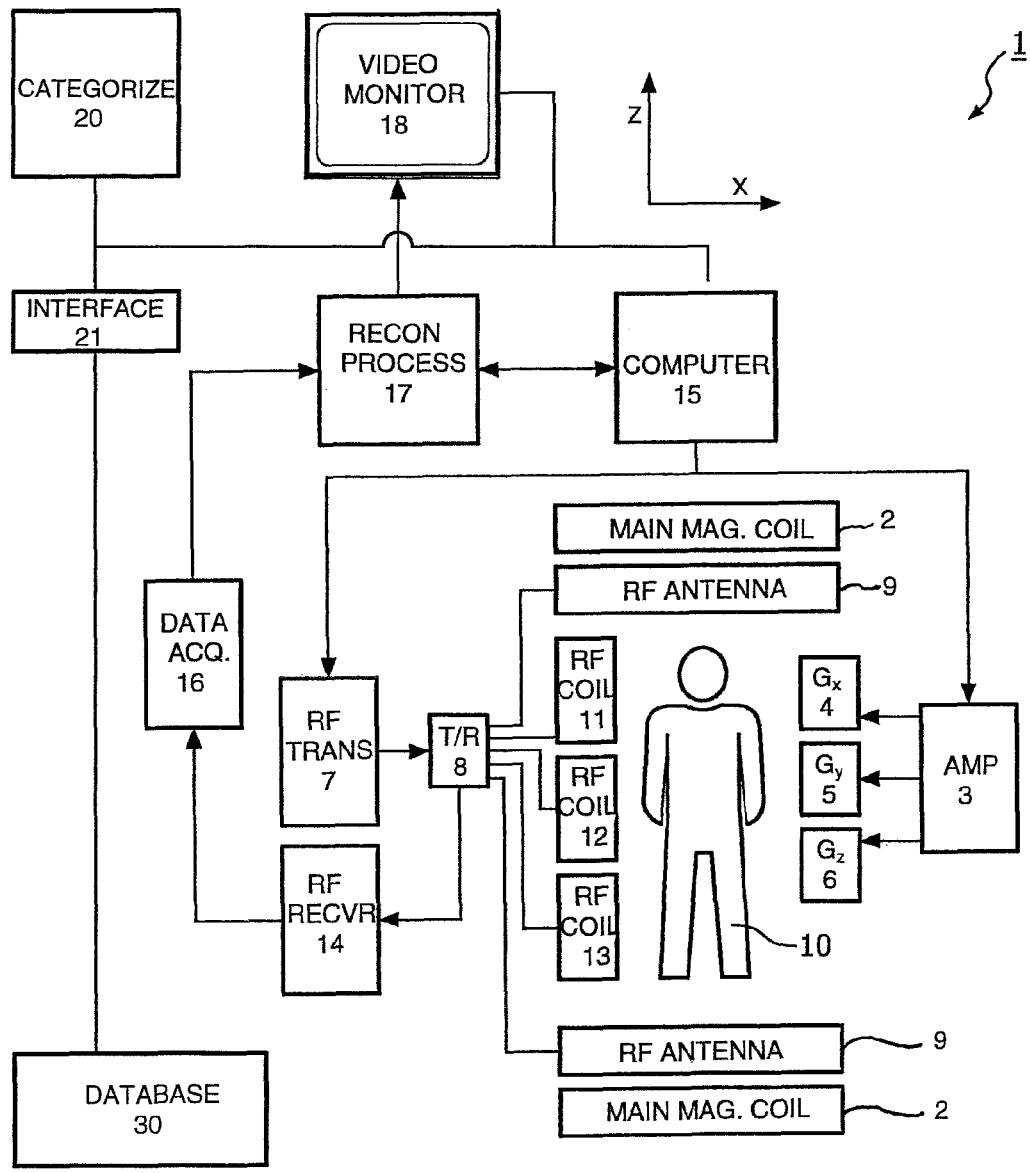
FIG. 1 illustrates a schematic of an MR device according to the invention.

With reference to FIG. 1, an MR imaging system 1 is shown. The system comprises superconducting or resistive main magnet coils 2 such that a substantially uniform, temporarily constant main magnetic field BO is created along a z-axis through an examination volume.

The magnetic resonance system applies a series of RF pulses and switched magnetic field gradients to invert or excite nuclear magnetic spins, induce magnetic resonance, refocus magnetic resonance, manipulate magnetic resonance, spatially or otherwise encode the magnetic resonance, saturate spins and the like to perform MR imaging.

More specifically, a gradient pulse amplifier 3 applies current pulses to selected ones of whole body gradient coils 4, 5 and 6 along x, y and z-axes of the examination volume.

An RF transmitter 7 transmits RF pulses or pulse packets, via a send/receive switch 8 to an RF antenna 9 to transmit RF pulses into the examination volume. A typical MR imaging sequence is composed of a packet of RF pulse sequences of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals may also be picked up by the RF antenna 9.

For generation of MR images of limited regions of the body or in general object 10, for example by means of parallel imaging, a set of local array RF coils 11, 12 and 13 are placed contiguous to the region selected for imaging. The array coils 11, 12 and 13 can be used to receive MR signals induced by RF transmissions effected via the RF antenna. However, it is also possible to use the array coils 11, 12 and 13 to transmit RF signals to the examination volume.

The resultant MR signals are picked up by the RF antenna 9 and/or by the array of RF coils 11, 12 and 13 and are demodulated by a receiver 14 preferably including a pre-amplifier (not shown). The receiver 14 is connected to the RF coils 9, 11, 12 and 13 via a send/receive switch 8.

A host computer 15 controls the gradient pulse amplifier 3 and the transmitter 7 to generate any of a plurality of imaging sequences, such as echo planar imaging (EPI), echo volume imaging, gradient and spin echo imaging, fast spin echo imaging and the like.

For the selected sequence, the receiver 14 receives a single or a plurality of MR data lines in a rapid succession following each RF excitation pulse. A data acquisition system 16 performs analogue to digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms. The MR image may represent a planar slice through the patient, an array of parallel planar slices, a three-dimensional volume or the like. The image is then stored in an image memory where it may be accessed for converting slices or other portions of the image representation into appropriate formats for visualization, for example via a video monitor 18 which provides a man readable display of the resultant MR image.

Further shown in FIG. 1 is an interface 21 connected to for example the host computer 15. The interface 21 serves for providing a communication with an external database 30. As described above, in case an MR imaging protocol is received for example via the user interface 18, the host computer 15 may either provide directly this MR imaging protocol via the interface 21 to the database 30, wherein in response to the provision of said protocol the database 30 returns statistical information comprising statistics on modification of individual scan parameters with respect to said provided MR imaging protocol.

Alternatively, the host computer 15 may provide the MR imaging protocol to the categorizing component 20, which categorizes the MR imaging protocol into an MR scan type of a predefined set of MR scan types, wherein this identified MR scan type is then provided via the interface 21 to the database 30.

In the following, these principles shall be discussed in greater detail with respect to the block diagram in FIG. 2 which illustrates various method steps with respect to the present invention.

Shown in FIG. 2 is for example a user interface, for example a graphical user interface 18, which displays various parameters of a selected MR imaging protocol. For example, an MR imaging protocol may be stored in a database (not shown in FIG. 2) comprising so called 'ExamCards', where scan protocols are optimized and stored according to the most often performed examinations with respect to the scanner 1 shown in FIG. 2.

However, scan protocols require adaption of a certain number of parameters to comply with patient-specific constraints. In the state of the art this is generally done by a radiology technician during the examination, while the patient is on the scan table, wherein the technician often has to cope with patient-specific problems such as motion or breathe hold length. It turned out that not only geometry parameters are routinely adapted by the technician but also parameters having an influence on image quality, scan time or contrast. The degree to which scan parameters are optimized by the user greatly varies within institutions or technicians.

Examples of user interface parameters requiring more or less frequent adaption by a technician include for example the field of view, resolution, number of slices, slice gap, fold over direction, SENSE mode, SENSE reduction factor, number of averages, echo time and repetition time.

The present invention uses for example data-mining techniques to find out which parameters of a given scan protocol require adaption and to provide statistical information on the values they are typically used with. The database system 30 uses log files 104 that are systematically for example stored on the MR system and sent to the database system 30 via a remote service network. These log files 104 contain the values of all user interface parameters for previously executed MR scans. The main advantage of using the log files as an information source is that parameter settings often encountered in practice are taken as a basis, as opposed to rule-based mechanisms.

In the simplest form, the invention exploits the log files stemming from the MR system under consideration. However, generally it is preferred to use log files from a multitude of different MR systems and to build up a database which offers multi-site information.

In a preprocessing step 106 the values of the scan parameters are extracted from the log files 104 and are organized in a database table 100 at the database system 30.

However, it has to be noted here that the present invention can also be carried out by using for example only a local database system 30 associated with the MR scanner shown in FIG. 2. In this case, the database table 100 is a local database table and not a global one as discussed above. In case the database system is a local database system, the values of the scan parameters may be extracted and stored in a local database table 100 of the MR system 1, possibly as a compliment to the ExamCard database.

However, without loss of generality in the following it is assumed that the database system 30 is a global database system at a remote site compared to the MR scanner used in FIG. 2. Data transmission between the MR scanner 1 and the database system 30 may be performed via a network like the internet.

For each scan protocol contained in the database table 100, the database system 30 computes statistics on the scan parameters which are most frequently adapted for this particular protocol, together with statistical descriptors of the parameter values such as the modes (most frequent values) or the range. For this purpose, the information comprised in the log files 104 may be parsed in a suitable data structure, containing only the relevant parameters. For example this data structure may be an XML data structure. The results of the parsing operation are then stored into the database table 100. Preferably, the database system 30 collects information gathered over multiple days or weeks, and possibly from different installed scanners. Besides scan protocol parameters, the database may also store information on hardware and software configuration for each scan protocol like the scanner type, hardware configuration such as gradient type and software release number.

The search for optimized protocol settings becomes active on the MR scanner 1 when an MR user loads a protocol from the ExamCard database into the scan lists and starts editing the protocol in the for example graphical user interface 18. Upon loading the protocol from the ExamCard, either the loaded protocol or an MR scan type into which the loaded MR imaging protocol is categorized is provided to the database system 30, which in turn provides statistical information 102 on this specific MR scan type to the scanner. The data-mining performed by the database system 30 on the database table 100 may be either performed 'on the fly' when receiving the MR scan type or the MR imaging protocol. Alternatively the data-mining may be performed in a preprocessing step such that the database system 30 only has to access the readily computed statistical information on the MR scan type. In the latter case, the statistical information is precomputed.

Then, the statistical information is provided in step 108 to the graphical user interface 18. Herein, different functionalities may be provided at the graphical user interface 18:

For example a set of scan parameters which often require adaption may be displayed. These parameters may be grouped into a single parameter group or just highlighted in the whole parameter list on the graphical user interface. Further, it is possible to display statistics showing the typical values (mode or range) for a selected parameter. This functionality could become active for example only upon request by the user. Alternatively, this functionality may become active automatically in case a user starts editing a selected parameter. The statistics can be derived from the pre-computed statistics, or they may be computed on the fly, taking into account the values of all other scan parameters currently chosen.

A further functionality may be displaying of a warning (or request for confirmation) for parameters being out of the typical range of utilization, once the protocol has been finalized.

Consequently, the invention provides a method which permits the technician to identify in an easy and reliable manner which parameters of a given MR scan protocol may require adaption and which parameter values may be appropriate for that purpose. It has to be noted that categorizing of an MR imaging protocol into an MR scan type may be performed at different levels of complexity: categorization may be either performed, as described above, only with respect to a given type of imaging sequence which describes in a generic term different sub-groups of specialized imaging pulse sequences. However, it is additionally or alternatively possible to perform a categorization with respect to desired imaging contrast types or even with respect to specific applications.

After completion of an MR scan, the logfile 104 generated by the MR system 1 upon execution of the MR scan is provided to the database system 30 for further analysis, i.e. for enabling updating the database table 100 and optionally the statistical information 102.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of performing a magnetic resonance imaging scan using an MR scanner, the method comprising the acts of:
receiving an MR imaging protocol via a user interface, the MR imaging protocol being associated with a selected MR scan type from a predefined set of MR scan types, wherein the MR imaging protocol includes adjustable parameters of the MR scanner that are configured for performing the MR imaging scan using the selected MR scan type employed at the MR scanner when performing the MR imaging;
querying a database with a processor by providing the received MR imaging protocol into the database regarding the selected MR scan type and analyzing, with the processor, a plurality of the MR imaging protocols of the selected MR scan type that had been previously stored in the database and data mining statistical information, about the adjustable parameters of the selected MR scan type;
receiving in response to said processor query, from the database, the data mined statistical information about the selected MR scan type, said data mined statistical information comprising statistics on a frequency and a range of adjustment of the adjustable parameters over the plurality of MR imaging protocols of the selected MR scan type that was queried in the database;
providing said data mined statistical information to the user interface;
receiving modifications of said MR imaging protocol, from the user interface, based on the data mined statistical information in order to generate a modified MR imaging protocol, and
performing the MR imaging scan using the modified MR imaging protocol.

2. The method of claim 1, wherein the data mined statistical information is based on information that had been previously stored in the database, about previously performed MR imaging scans employing said selected MR scan type.

3. The method of claim 2, wherein the act of providing said statistical information back to the user interface comprises indicating which individual scan parameters have data mined statistics in which a modification frequency is above a predefined threshold.

4. The method of claim 2, further including generating a graphical display illustrating the range and the frequency of values of the adjustable scan parameters stored in the database with respect to the selected MR scan type.

5. The method of claim 4, further comprising providing said graphical display on the user interface.

6. The method of claim 1, further comprising providing with the user interface values of the adjustable scan parameters of said modified MR imaging protocol into the database.

7. The method of claim 1, further comprising: analyzing with a computer/processor the received MR imaging protocol when obtaining an MR scan type of the selected imaging protocol.

8. A non-transitory computer readable medium comprising computer instructions which, when executed by a processor, configure the processor to perform the method as claimed in the claim 1.

9. A method of providing statistical information into a magnetic resonance imaging scanner that employs an MR scan type when performing an MR imaging scan, the method comprising:
receiving a query from a magnetic resonance imaging scanner in order to analyze with a computer/processor having a database a selected MR imaging protocol in order to identify the MR scan type of the selected MR imaging protocol;
wherein the MR imaging protocol includes adjustable scan parameters of the MR scanner that are of the selected MR scan type when performing the MR imaging scan;
data mining statistical information on the selected MR scan type, said data mined statistical information comprising statistics on a range and frequency of modifications made with respect to the values of individual ones of the scan parameters of the selected MR scan type, the data mined statistical information being based on information about previously performed MR imaging scans, that were performed employing said selected MR scan type; and
providing to the magnetic resonance imaging scanner said data mined statistical information.

10. A non-transitory computer readable medium comprising computer instructions which, when executed by a processor, configure the processor to perform the method of claim 9.

11. A system including a computer/processor and magnetic resonance (MR) imaging scanner configured for performing a magnetic resonance (MR) imaging scan, the computer/processor being configured to:
receive an MR imaging protocol via a user interface, the received MR imaging protocol being associated with a selected MR scan type from a predefined set of MR scan types, wherein the MR imaging protocol includes adjustable parameters of the MR imaging scanner that are configured for performing the MR imaging scan using the selected MR scan type, that is employed by the MR imaging scanner when performing the selected MR imaging scan;
query a database in order to provide the adjustable parameters at the database and data mining statistical information on the adjustable parameters of a plurality of MR imaging protocols of the selected MR scan type previously stored in the queried database;
receive in response to said processor query, from the database the data-mined statistical information on the selected MR scan type, said data-mined statistical information comprising statistics about modifications made with respect to individual ones of the adjustable parameters of the selected MR scan type found in the database;
providing said data mined statistical information to the user interface;
receive modifications to said MR imaging protocol, in order to generate a modified MR imaging protocol; and
control the MR scanner to perform the MR imaging scan using the modified MR imaging protocol.

12. The system of claim 11, wherein the data mined statistical information includes at least one of frequency and range of at least one of the adjustable parameters of the plurality of MR imaging protocols of the selected MR scan type that is/are stored in the database.

13. The system of claim 11, wherein the data mined statistical information includes a frequency and range of values of an individual one of the adjustable parameters of the plurality of MR imaging protocols of the MR scan type that are stored in the database.

14. The system of claim 13, wherein the data mined statistical information is depicted in a graphical format with a first axis indicative of the frequency of the database values and a second axis indicative of magnitude of the database values.

15. A data mining system that provides statistical information into a magnetic resonance (MR) imaging scanner, the system including:
   a database configured to store a plurality of MR imaging protocols used with a plurality of MR scan types, each MR imaging protocol including values of a plurality of individual adjustable scan parameters;
   a processor configured to:
      receive a query from the MR imaging scanner concerning adjustable scan parameters of a selected MR imaging protocol,
      analyze the identified MR imaging scan protocol in order to select an MR scan type of the selected MR imaging protocol,
      access the database in order to retrieve values of the adjustable scan parameters of a plurality of MR imaging protocols of the selected MR scan type,
      generate statistics about modifications made with respect to the values of individual ones of the scan parameters of the selected MR scan type, about previously performed MR imaging scans, that were performed employing said selected MR scan type; and
   a user interface configured to display the generated statistics about the modifications made with respect to the values of the individual scan parameters of the selected MR scan type.

16. The data mining system according to claim 15, wherein the generated statistics include:
   at least one of a frequency of occurrence of the values of at least one adjustable scan parameter and a range of the values of the same at least one adjustable scan parameter over the plurality of MR imaging protocols of the selected MR scan type that are stored in the database.

17. The data mining system of claim 15, wherein the generated statistics include a frequency and range of the values of individual ones of the scan parameters over the plurality of MR imaging protocols of the selected MR scan type that are stored in the database.

18. The data mining system of claim 17, wherein the generated statistics are depicted in a graphical format with a first axis indicative of the frequency of the database values and a second axis indicative of magnitude of the database values.

* * * * *